US00PP36836P3

(12) United States Plant Patent
Olesen

(10) Patent No.: US PP36,836 P3
(45) Date of Patent: Jul. 22, 2025

(54) ROSE PLANT NAMED 'Poulty036'

(50) Latin Name: *Rosa hybrida*
Varietal Denomination: Poulty036

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,191

(22) Filed: Sep. 5, 2024

(65) Prior Publication Data

US 2025/0107469 P1 Mar. 27, 2025

(30) Foreign Application Priority Data

Sep. 22, 2023 (QZ) ..... PBR 20231980

(51) Int. Cl.
*A01H 5/02* (2018.01)
*A01H 6/74* (2018.01)

(52) U.S. Cl.
USPC ..... Plt./117
CPC ..... *A01H 6/749* (2018.05)

(58) Field of Classification Search
USPC ..... Plt./118, 117
CPC ..... A01H 5/0222
See application file for complete search history.

*Primary Examiner* — Kent L Bell

(57) ABSTRACT

A new garden rose plant of the miniature class which has abundant, ivory flowers and attractive foliage. This new and distinct variety has shown to be uniform and stable in the resulting generations from asexual propagation.

2 Drawing Sheets

Botanical designation: *Rosa hybrida.*

Variety denomination: 'Poulty036'.

This application claims priority to Plant Breeder's Rights Application Number 2023/1980, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2016 and the resulting seeds were planted in a controlled environment in Fredensborg, Denmark. The new variety, named 'Poulty036', originated as a single seedling from the stated cross.

The new variety may be distinguished from its male pollen parent and female seed parent primarily by the following characteristics. The male pollen parent plant has white flowers while the new variety has ivory flowers. The female seed parent plant has apricot flowers while the new variety has ivory flowers.

The objective of the hybridization of this rose variety was to create a new and distinct variety with unique qualities, such as:

1. Uniform and abundant ivory flowers with long lasting quality;
2. Vigorous, but compact growth when propagated on its own roots;
3. Exceptional disease resistance.

This combination of qualities is not present in previously available commercial cultivars of this type, known to the inventor, and distinguish 'Poulty036' from all other varieties of which we are aware.

As part of the rose development program, Mogens N. Olesen germinated the seeds from the aforementioned hybridization during winter of 2016 and conducted evaluations on the resulting seedlings in a controlled environment in Fredensborg, Denmark. 'Poulty036' was selected in the spring of 2017 by the inventor as a single plant from the progeny of the aforementioned hybridization.

Asexual reproduction of 'Poulty036' by rooted cuttings was first done by Mogens N. Olesen in the nursery in Fredensborg, Denmark in July 2017. This initial and other subsequent asexual propagations conducted in controlled environments have demonstrated that the characteristics of 'Poulty036' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulty036'.

Specifically illustrated in FIG. 1 of the drawings are open flowers viewed from above and the side, a cluster of flower buds and partially opened flower, and sepals detached revealing reproductive flower parts.

Figure 1:
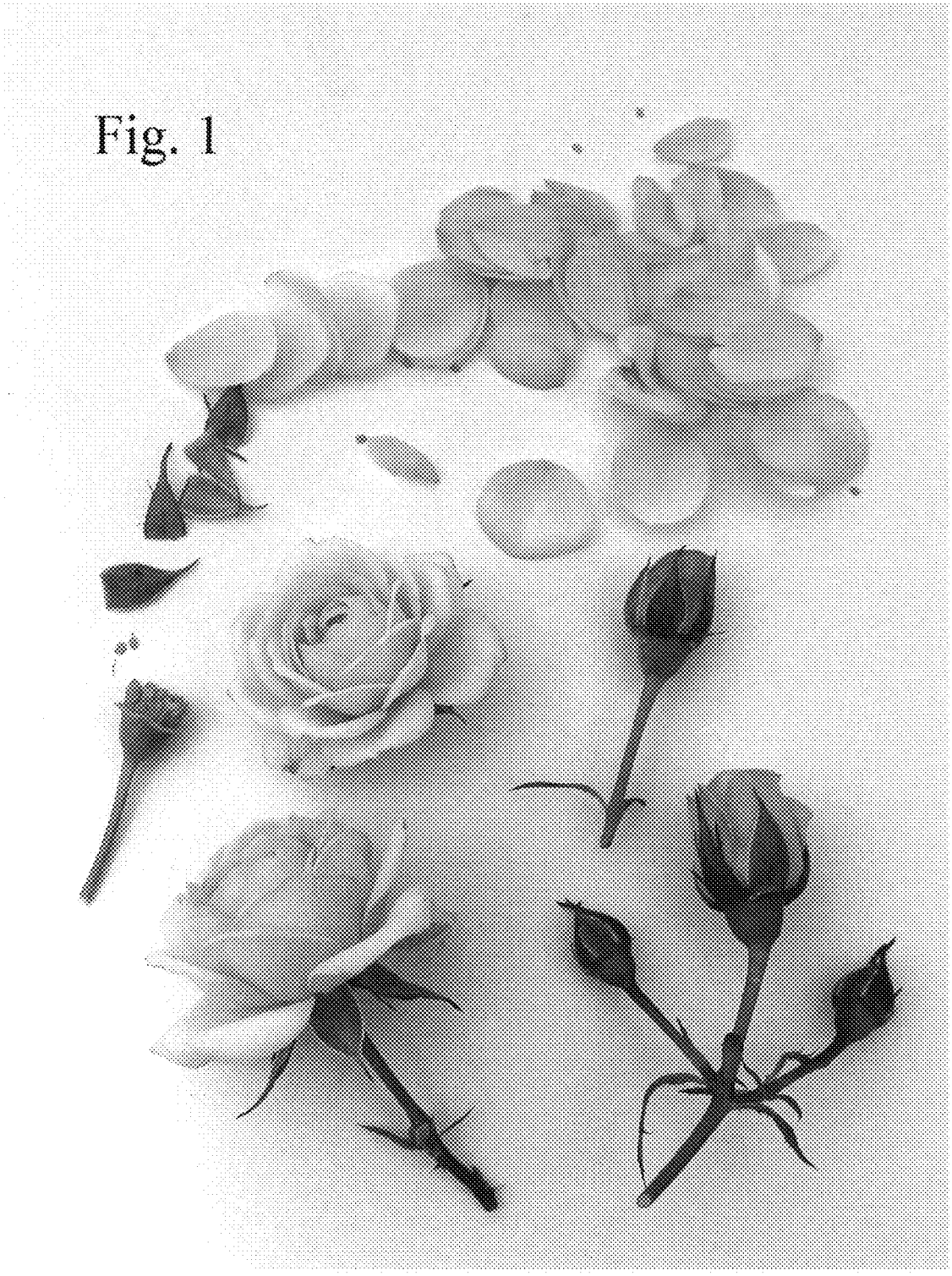
Figure 2:
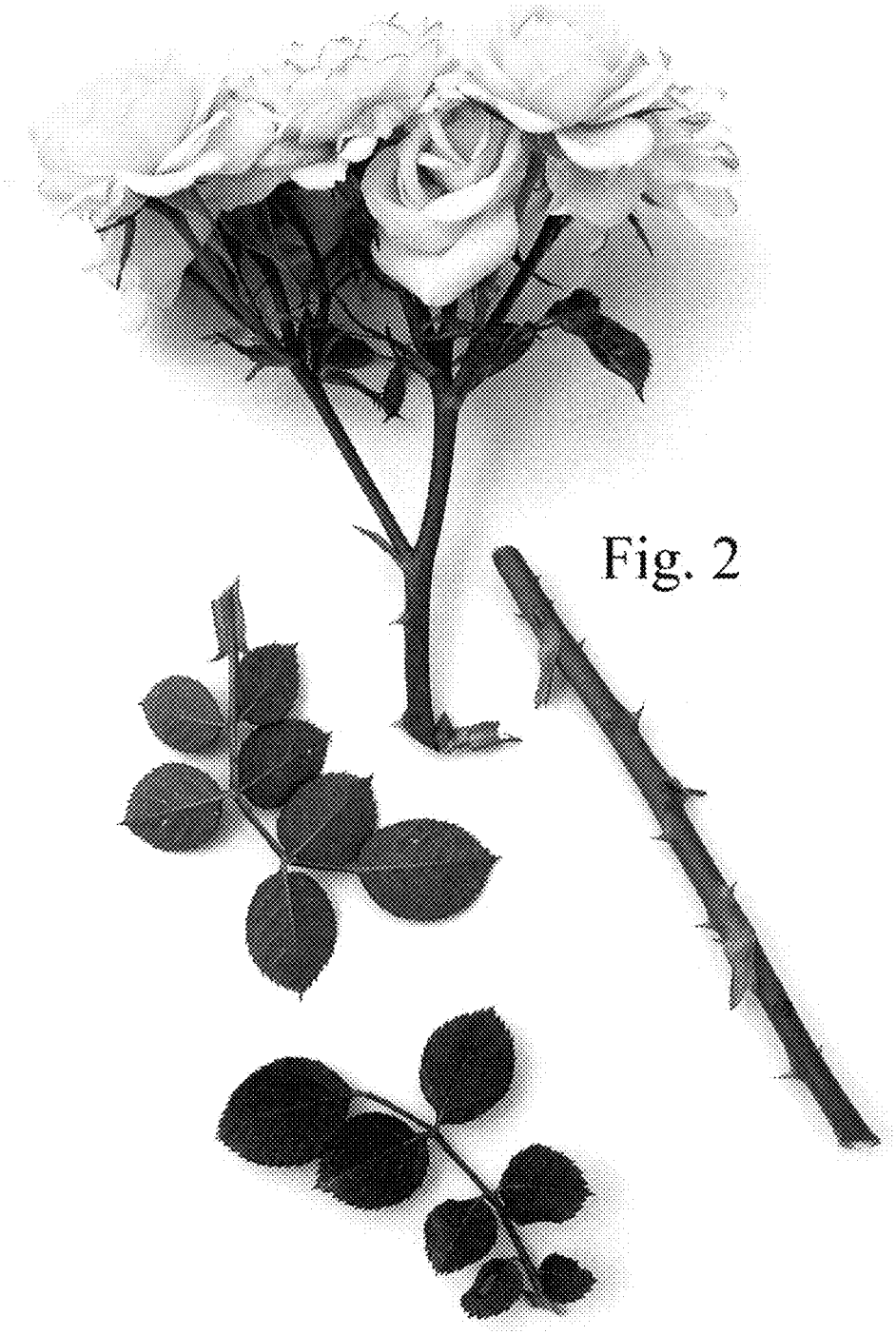

Specifically illustrated in FIG. 2 of the drawings are a cluster of open flowers on a branch, a bare stem exhibiting prickles, and mature leaves viewed from above and underneath. Plants shown are 12 months old.

DETAILED DESCRIPTION OF THE VARIETY

The following is a description of 'Poulty036', as observed in its growth in an outdoor nursery in Half Moon Bay California. Observed plants are 12 months of age, and were grown on their own roots in 24 cm pots. Color references are made using The Royal Horticultural Society (London, England) Colour Chart, 2001, except where common terms of color are used.

For a comparison, several physical characteristics of the rose variety 'Poulty015', U.S. Plant Pat. No. 26,017 are compared to the claimed plant. While 'Poulty036' has 50 flower petals, 'Poulty015' has 75 flower petals. Open flowers of 'Poulty036' have a general tonality of Orange-White Group 159D, Yellow-Orange Group 16C, and Yellow-Orange Group 20B, while the general flower color of 'Poulty015' is Yellow Group 10C with intonations of Yellow-Orange Group 23C.

FLOWER AND FLOWER BUD

Blooming habit: Continuous.

Flower bud:

*Size.*—Upon opening, 20 mm in length from base of receptacle to end of bud. Bud diameter is 10 mm.

*Bud form.*—Ovoid.

*Bud color.*—As sepals divide petals are Orange-Red Group 31A and Yellow-Orange Group 16C.

*Sepal inner surface.*—Color: Yellow-Green Group 146D. Surface: Lightly pubescent.

*Sepal outer surface.*—Color: Yellow-Green Group 144A with intonations of Greyed-Red Group 180A. Texture: Smooth.

*Sepal shape.*—Subulate. Apex: Caudate. Base: Flat at union with receptacle.

*Sepal margin.*—Margins have weak foliaceus appendages on three of the five sepals.

*Sepal size.*—About 25 mm long by 7 mm wide.

*Receptacle.*—Texture: Smooth. Size: 4 mm in height, 6 mm wide. Color: Yellow-Green Group 144A. Shape: Campanulate.

*Pedicel.*—Surface: Smooth. Length: 20 mm. Diameter: 3 mm on average. Color: Yellow-Green Group 144A Greyed-Red Group 180A. Strength: Strong.

*Peduncle.*—Length: 20 to 30 mm. Diameter: About 3 mm. Color: Yellow-Green Group 144A Greyed-Red Group 180A. Texture: Smooth.

Flower bud development: Flower buds are borne in clusters of 3 to 5 flower buds per stem.

Flower bloom:

*Fragrance.*—Moderate honey like perfume.

*Duration.*—The blooms have a duration on the plant of approximately 21 days. Petals fall cleanly away from plant after flowers have fully matured.

*Size.*—Flower diameter is 50 mm when open. Flower depth is 23 mm.

*Flower shape.*—Cup shaped with a center which is tightly closed.

*Shape of flower, side view.*—The upper portion is flat. The lower portion is flat convex.

Petalage: Under normal conditions, flowers have about 50 petals.

General tonality of flower: Open flowers are Orange-White Group 159D, with other blending of Yellow-Orange Group 16C and Yellow-Orange Group 20B intonations.

Petal color:

*Upon opening, outer and inner petals.*—Upper surface: Yellow Group 13D with intonations of Yellow Group 12B at the basal zone. Lower surface: Yellow-Orange Group 18C with intonations of Yellow Group 10A at the basal zone.

*After opening, outer and inner petals.*—Upper surface: Yellow Group 4D at marginal zone and Yellow Group 3C at the basal zone. Lower surface: Yellow Group 4D at marginal zone and Yellow Group 3C at the basal zone.

Petals:

*Petal reflex.*—Lightly reflexed.

*Margin.*—Entire and uniform. Moderate undulations.

*Shape.*—Round or elliptic. Apex shape: Rounded. Base shape: Acute.

*Size.*—About 20 mm (l)×20 mm (w).

*Texture.*—Smooth on upper and lower surface.

*Thickness.*—Average.

Petaloids:

*Size.*—12 mm (l) by 8 mm (w).

*Quantity.*—About 5.

*Shape.*—Elliptical with an acute base and rounded apices.

*Color.*—The upper surface is Yellow Group 13D with intonations of Yellow Group 12B at the basal zone. The lower surface is Yellow-Orange Group 18C with intonations of Yellow Group 10A at the basal zone.

Reproductive flower parts:

*Pollen.*—None observed.

*Anthers.*—Size: 2 mm in length. Color: Greyed-Orange Group 163B. Quantity: 65 on average.

*Filaments.*—Color: Yellow Group 13B. Length: 3 mm.

*Pistils.*—Length: 4 mm. Quantity: 30 on average.

*Stigmas.*—Color: Yellow-Green Group 145D.

*Styles.*—Color: Yellow-Green Group 145D with intonations of Red Group 56A.

*Location of stigmas.*—Level in location relative to the length of the filaments and the height of the anthers.

*Hips.*—None Observed.

PLANT

Plant growth: Upright, bushy. Plants are 27 cm in height, and 38 cm wide.

Stems:

*Color of juvenile growth.*—Yellow-Green Group 144B.

*Color of mature growth.*—Yellow-Green Group 144A.

*Length.*—Canes are about 10 cm from the base of the plant to the flowering portion.

*Diameter.*—About 5 mm.

*Internodes.*—On mature canes about 30 mm between nodes.

*Surface texture.*—Young wood: Smooth. Older wood: Smooth.

Long prickles:

*Incidence.*—About 13 prickles per 10 cm of stem.

*Size.*—Average length of prickles on mature stems is 4 mm.

*Shape.*—Upper portion is linear. Lower portion is concave.

*Color.*—Juvenile prickles: Greyed-Red Group 180C. Mature prickles: Greyed-Red Group 180C.

Plant foliage:

*Compound leaf.*—About 95 mm (l)×47 (w).

*Quantity.*—3 leaves per 10 cm of stem on average.

*Leaf bearing angle to the stem.*—45 degrees.

*Color of juvenile foliage*.—Upper side: Yellow-Green Group 144A. Lower side: Yellow-Green Group 144B.

*Color of mature foliage*.—Upper side: Yellow-Green Group 146A. Lower side: Yellow-Green Group 146B.

Plant leaves and leaflets:

*Stipules*.—Size: 11 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 21 mm. Diameter: 1.5 mm. Upper surface color: Yellow-Green Group 144A. Lower surface color: Yellow-Green Group 144A. Texture: The upper surface is glandular. The lower surface is smooth.

*Rachis*.—Length: About 45 mm. Diameter: 1.5 mm. Upper surface color: Yellow-Green Group 144A. Lower surface color: Yellow-Green Group 144A. Texture: The upper surface is glandular and smooth. The lower surface has three to 4 small prickles.

*Leaflet*.—Quantity: Normally 7 leaflets. Margins: Serrated. Size: Terminal leaflets are about 30 mm long, 21 mm wide. Shape: Generally elliptical. Base: Rounded. Apex: Mucronate. Texture: Smooth at the lower and upper surface. Thickness: Average. Arrangement: Odd pinnate. Venation: Reticulate. Glossiness: The upper surface is moderately glossy. The lower surface is not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

Pest resistance: The variety is susceptible to ordinary pests that affect the species.

I claim:

1. A new and distinct variety of rose plant named 'Poulty036' substantially as described and illustrated herein.

* * * * *